United States Patent
Merade et al.

(10) Patent No.: US 7,431,690 B2
(45) Date of Patent: Oct. 7, 2008

(54) IMPLANTABLE SLING FOR THE TREATMENT OF MALE INCONTINENCE AND METHOD OF USING THE SAME

(75) Inventors: Bryon L. Merade, Thousand Oaks, CA (US); Craig Comiter, Tucson, AZ (US); Victor Nitti, Wycoff, NJ (US); Raymond Rackley, Shaker Heights, OH (US); Eugene Rhee, San Diego, CA (US); Sandip Vasavada, Westlake, OH (US); Kapri Ellenson, Los Alamitos, CA (US)

(73) Assignee: Coloplast A/S, Humlebaek (DK)

( * ) Notice: Subject to any disclaimer, the term of this patent is extended or adjusted under 35 U.S.C. 154(b) by 96 days.

(21) Appl. No.: 11/119,446

(22) Filed: Apr. 30, 2005

(65) Prior Publication Data

US 2006/0247490 A1 Nov. 2, 2006

(51) Int. Cl.
*A61F 2/02* (2006.01)
(52) U.S. Cl. ............................................. 600/30
(58) Field of Classification Search ............ 600/29–32; 128/897, 898, DIG. 25
See application file for complete search history.

(56) References Cited

U.S. PATENT DOCUMENTS

| | | | | |
|---|---|---|---|---|
| 4,009,711 | A | * | 3/1977 | Uson ........................... 600/40 |
| 5,230,694 | A | * | 7/1993 | Rosenblum .................. 600/40 |
| 5,899,909 | A | | 5/1999 | Claren et al. |
| 6,050,937 | A | | 4/2000 | Benderev |
| 6,200,330 | B1 | | 3/2001 | Benderev |
| 6,273,852 | B1 | | 8/2001 | Lehe et al. |
| 6,302,840 | B1 | | 10/2001 | Benderev |
| 6,328,686 | B1 | | 12/2001 | Kovac |
| 6,491,703 | B1 | | 12/2002 | Ulmsten |
| 6,638,211 | B2 | | 10/2003 | Suslian et al. |
| 6,685,626 | B2 | | 2/2004 | Wironen |
| 6,808,486 | B1 | | 10/2004 | O'Donnell |
| 6,884,212 | B2 | | 4/2005 | Thierfelder et al. |
| 2002/0161382 | A1 | | 10/2002 | Neisz et al. |
| 2002/0188169 | A1 | | 12/2002 | Kammerer et al. |
| 2003/0023138 | A1 | | 1/2003 | Luscombe |
| 2003/0171644 | A1 | | 9/2003 | Anderson et al. |
| 2003/0176762 | A1 | * | 9/2003 | Kammerer ................... 600/30 |

(Continued)

OTHER PUBLICATIONS

International Search Report, PCT/US06/16709, dated Apr. 4, 2007.

(Continued)

*Primary Examiner*—Samuel G Gilbert
(74) *Attorney, Agent, or Firm*—Inskeep Intellectual Property Group, Inc.; Walter K. Roloff

(57) ABSTRACT

An implantable sling for the treatment of male incontinence and method of Implementing the same. The sling comprises a urethral support portion and at least one anchoring portion extending therefrom. The anchoring portion is operatively positioned through the obturator foramen and about at least one ramus portion of the pelvis such that the support portion of the implant is operatively positioned at or distal to the bulbar urethra to treat urinary incontinence. In a preferred embodiment, the implant will have first and second anchoring portions extending from the support portion with each respective one of said anchoring portions being operative to be secured about dedicated ones of the patient's pubic ramus. The implants may further be fabricated from tissues, synthetic materials or combinations thereof.

20 Claims, 3 Drawing Sheets

U.S. PATENT DOCUMENTS

2003/0216814 A1* 11/2003 Siegel et al. ............. 623/23.66
2004/0039453 A1   2/2004  Anderson et al.
2004/0143152 A1   7/2004  Grocela
2005/0027160 A1   2/2005  Siegel et al.

OTHER PUBLICATIONS

Kobashi, K., S. Mee, G. Leach; A New Technique for Cystocele Repair and Transvaginal Sling: The Cadaveric Prolapse Repair and Sling (CaPS); Elsevier Science Inc.; Dec. 2000; p. 9-14.

Chon, J.; Bodell, D.; Kobashi, K.; and Leach, G. Results of the Transvaginal Cadaveric Prolapse Repair with Sling (CAPS). Urology. Dec. 4, 2000; 56(6 Suppl 1): 9-14.

Kobashi, K., and Govier, F. Virginia Mason Med. Ctr. The Use of Solvent-Dehydrated . . . J. Urol. 2002;167(4):78, Abstr. #309, AUA 97th Ann. Mtg., Orlando, FL, May 26, 2002.

Almeida, S.H.M., et al. Use of Cadaveric Fascia Lata to Correct Grade IV Cystocele. Official J. Brazilian Soc. Urol. Jan.-Feb. 2003. p. 48, et seq.

* cited by examiner

IMPLANTABLE SLING FOR THE TREATMENT OF MALE INCONTINENCE AND METHOD OF USING THE SAME

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention is directed to surgical implants for the treatment of male incontinence, and in particular, implantable slings that are operative to provide sling-type support at or distal to the bulbar urethral region of a patient and operatively anchored into position via fixation about the patient's descending rami.

Of the estimated 19 million North American adults who have urinary incontinence, 20% are estimated to be men. Such condition can range in severity from partial to complete loss of bladder control and patients afflicted with urinary incontinence can experience varying degrees of urine loss. In addition, it is known that urinary incontinence may change over time and that men with light incontinence, for example, may experience minimal leakage during the occurrence of a provocative event, such as laughing or coughing, whereas men with heavy incontinence may experience continuous urine leakage.

Generally, male urinary incontinence is not considered a disease, but rather a symptom or side effect of another medical condition. Among the causes known to cause urinary incontinence include prostate surgery, and in particular total prostatectomy, head and spinal cord injury, infection, certain toxins, such as too much alcohol consumption, certain medications, such as sedating medications, and certain diseases, such as cancer, Parkinson's disease and multiple sclerosis. Indeed, male incontinence can be caused simply by virtue of the aging process or emotional distress.

Each case of male incontinence, however, is unique and no two men are affected by incontinence in the same way. There are, however, well-recognized types of incontinence and various ways to treat the same. Stress incontinence, which is the most common type of incontinence, wherein urine leakage occurs during the occurrence of a provocative event, such as sneezing, laughing, lifting heavy objects, or when the patient engages in any type of exercise that puts pressure on the bladder. Urge incontinence occurs when the patient wants to urinate but is incapable of exercising restraint until reaching a restroom. Additional types of incontinence include overflow incontinence, which occurs when the quantity of urine exceeds the capacity of the patient's bladder, and functional incontinence, which occurs when the patient has knowledge of the need to urinate but simply cannot access a restroom quickly enough due to a physical obstruction or debilitation.

To treat male urinary incontinence, several options are available. Among the more effective types of recognized treatment include behavioral techniques, such as biofeedback, bladder training, and pelvic muscle exercises, and modifications of the patient's diet and fluid intake. With respect to the latter, it is known that eliminating or cutting back on certain types of substances, such as caffeine and alcohol, can help alleviate incontinence. There are additionally medications available, such as dicyclomine (Bentyl), flavoxate (Urispas), hyoscyamine sulfate (Anaspaz), imipramine (Tofranil), oxybutynin (Ditropan), tolterodine (Detrol), and propantheline (Pro-Banthine), phenylpropanolamine (Dexatrim), and pseudoephedrine (Sudafed) that are helpful in controlling urinary incontinence.

Surgery may additionally be an option to treat male urinary incontinence. Along these lines, surgical implants, such as the In-Vance, produced by American Medical Systems, Inc., of Minneapolis, Minn., is a commercially available surgical implant that is operative to provide structural support to the urethra for the treatment of stress incontinence. In this regard, the implant is operative to provide structural support to the urethra such that during a provocative event, the implant will provide structural support to the urethra thus causing the urine to be retained within the bladder and not leak through the urethra.

With respect to utilizing sling implants to treat male incontinence, however, such approach has numerous drawbacks. Due to the differences between male and female anatomy, to secure suburethral sling implants into position typically requires the use of bone screws, which are well-known in the art to be difficult and time consuming to deploy, and can result in significant patient discomfort, especially within the first couple of weeks following the surgical implantation. In addition, implanting suburethral slings are often times difficult to secure into position with the optimal degree of tension. Indeed, the implantation of suburethral slings for the treatment of male incontinence is well-recognized as complex, time consuming and can produce suboptimal clinical outcomes. Moreover, it is well recognized among urologists performing such implant procedures that sutures attached to bone anchors and or bone screws utilized to secure the sling into position frequently break and that often times additional bone screws must be secured into position. In fact, each suture attached to bone anchors and or bone screws must typically be retensioned two to three times before optimal sling positioning and structural support to the urethra is achieved.

Accordingly, there is a substantial need in the art for a suburethral sling implant for the treatment of male incontinence that is substantially easier to surgically secure into position and that can further provide an optimal degree of urethral support to thus effectively treat male urinary incontinence. There is additionally a need in the art for an implant that is of simple construction, easy to surgically manipulate, and can be manufactured at relative low cost utilizing known implant materials, whether it be synthetic materials, natural tissues, or combinations thereof. There is yet a further need in the art for such an implant that can be secured into position such that the implant defines a suburethral sling portion operatively positioned at or distal to the bulbar urethra of the patient that remains anchored into position via the use of an anchoring portion that extends through the obturator foramen and remain secured at or near the descending rami of the patient's pelvis without the use of bone anchors. With respect to the latter, it would be exceptionally advantageous for such a surgical implant that could be anchored to the pubis through the obturator foramen preferably via the descending rami thereof.

BRIEF SUMMARY

The present invention specifically addresses and alleviates the above-identified deficiencies in the art. In this regard, the present invention is directed to suburethral sling implants and methods of deploying the same that are effective and substantially easier to deploy than prior art implants and implantation techniques for treating male incontinence. The implant comprises the combination of a urethral support portion and at least one anchoring portion. The support portion is operatively positioned at or distal to the bulbar urethra. Per conventional suburethral slings, the support portion is operative to provide structural support to the urethra such that during the occurrence of a provocative event, the sling is operative to compressively engage the urethra to prevent urine leaking therefrom. The support portion will have a surface area that is at least 2 cm long by 1 cm wide to 8 cm long by 8 cm wide.

The anchor portion extends from the support portion. The anchor portion, which may take a variety of configurations, is operative to extend through the obturator foramen of the patient and become secured at a locus preferably at or near the descending ramus. To effectuate such attachment, it is contemplated that one or more sutures may be utilized to ensure that the anchor portion becomes secured about the ramus and that the support portion remains operatively positioned at or distal to the bulbar urethra. In a preferred embodiment, the implant will have at least two anchor portions extending from the support portion with each respective anchor portion extending through the obturator foramen and attachable about respective ones of the patient's rami. The anchor portions will have a width ranging from between 0.5-4 cm and the length ranging from at least 5.0 cm to 45.0 cm. To the extent necessary, both the support and anchor portions of the implant may be surgically fashioned as necessary to optimize sizing and configuration of the implant to suit the needs of a specific patient.

In certain embodiments of the implant of the present invention, the same may take the form of implants having a central support structure with anchoring portions extending therefrom in opposed directions or may be fashioned to have generally "H", inverted "U", or "X" shapes. The implants may further be provided as generally rectangular, square or trapezoidal shapes and may further be provided with one or more apertures to accommodate the attachment of sutures, surgical tacks and the like. The implants of the present invention may further be fabricated such that sutures are pre-attached thereto, per the teachings of Applicants' co-owned pending U.S. patent application Ser. No. 10/947,182, entitled READILY IMPLANTABLE SLING, filed Sep. 22, 2004, the teachings of which are expressly incorporated by reference. The implants of the present invention may further be fabricated from any of a variety of surgically compatible materials well-known in the art, including synthetic materials, such as synthetic mesh and the like, as well as natural materials, such as harvested tissues from sources such as animals, cadavers or the patient himself. The implants may further be fabricated such that the same are formed from combinations of materials, including but not limited to combinations of different types of synthetic materials, combinations of different types of natural tissues and/or combinations of both synthetic and natural tissues.

Regardless of the embodiment, in all procedures involving the implantation of the implants of the present invention, such procedures are performed with the patient assuming a lithotomy position. A vertical perineal incision is made in the midline dissecting to expose the bulbar urethra and the inferior aspect of the descending rami bilaterally. A surgical introducer is utilized to introduce the implant into position, typically through the obturator foramen, in a manner that is substantially easier and less traumatic than conventional surgical procedures utilized to access and implant slings for the treatment of male incontinence. Once the surgical site is accessed and the anchoring portion will preferably be positioned through the obturator foramen and anchored into position. Surgical sutures and the like may be deployed to facilitate anchoring of the anchor portions of the implant. Minor variations well-known to those skilled in the art may necessarily be made to effectuate optimal attachment and positioning of the support portion of the implant, as may be necessary for a given patient. In all cases, however, the surgical procedures and implants of the present invention provide a radically more efficient, effective and less traumatic surgical approach to the treatment of male incontinence.

BRIEF DESCRIPTION OF THE DRAWINGS

These and other features and advantages of the various embodiments disclosed herein will be better understood with respect to the following description and drawings, in which like numbers refer to like parts throughout.

DETAILED DESCRIPTION

The above description is given by way of example, and not limitation. Given the above disclosure, one skilled in the art could devise variations that are within the scope and spirit of the invention disclosed herein, including various ways of making and surgically implanting the implants described herein. Further, the various features of the embodiments disclosed herein can be used alone, or in varying combinations with each other and are not intended to be limited to the specific combination described herein. Thus, the scope of the claims is not to be limited by the illustrated embodiments.

Figure 1:
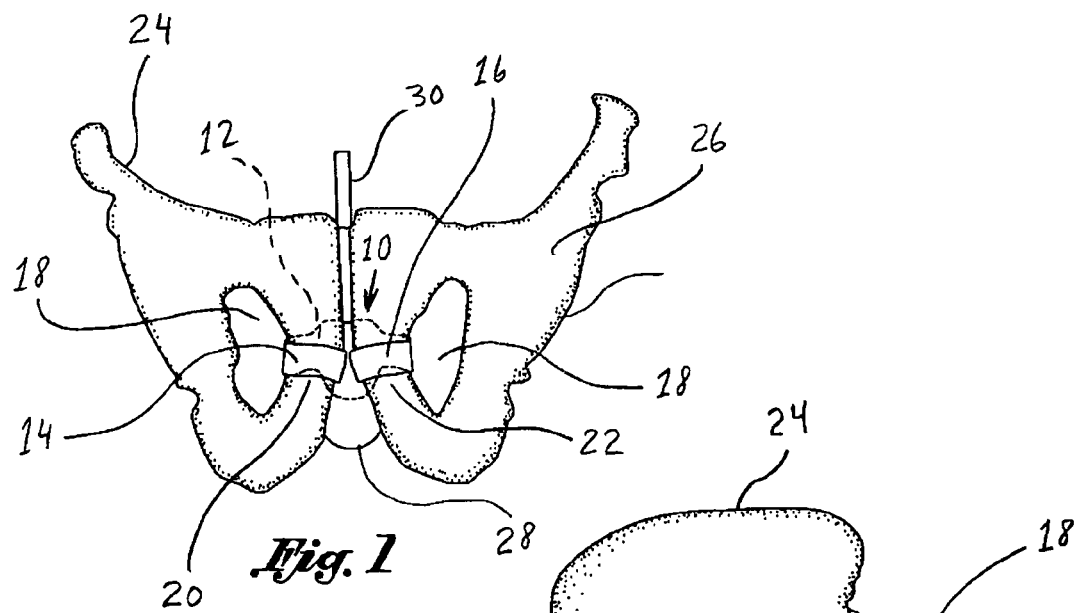
FIG. 1 is a frontal perspective view of a pelvis, a bladder and a urethra extending therefrom with a sling-type implant shown operatively secured into position, the implant having a support portion aligned at or distal to the bulbar urethra and anchoring portions, the latter shown extending through the obturator foramen and secured about dedicated ones of the rami of each hip bone.

Referring now to the drawings, initially to FIG. 1, there is shown an implant 10 for the treatment of male incontinence that is operative to provide suburethral support to thus prevent the leakage of urine, particularly when the patient experiences a provocative event. In this respect, the implant 10 is operative to act as a suburethral sling, as is known in the art, but is advantageously operative to be more easily secured into position than prior art sling implants. The implants of the present invention are further capable of being deployed in a manner that is far less traumatic than prior art sling implants and methods of surgically implanting the same, and further utilizing novel attachment approach that provides for optimal suburethral positioning of the sling 10 in an exceptionally secure manner without the use of bone anchors.

In its broadest sense, the implants of the present invention comprise the combination of a urethral support portion and at least one anchoring portion. The support portion is operatively positioned at or distal to the bulbar urethra. The anchoring portion is operative to secure the support portion into position to thus provide structural support to the urethra, and particularly so during the occurrence of a provocative event. To achieve that end, the anchoring member is generally operative to extend through the obturator foramen and become secured at at least one and preferably both of the patient's rami. In preferred embodiments of the invention, discussed more fully below, the anchor portion will be operatively interconnectable with the descending ramus of one of the patient's pelvis. Advantageously, the positioning of the anchor portion against the descending ramus will be accomplished without the use of bone screws, which are well-known in the art to be problematic to deploy and utilized as an attachment point for sutures and the like.

The implants of the present invention further may take a variety of embodiments. In certain of the embodiments depicted, the implant will include first and second attachment portions extending from the support portion with each attachment portion being operatively extensible through the obturator foramen and attachable to respective ones of the patient's descending rami. Such attachment portions may be operative to extend in opposed directions from the support portion or, alternatively, extend in generally parallel relation to one another from the support portion. In certain other embodiments, the support portion anchoring portion may be formed as a continuous segment or otherwise formed to have a generally rectangular or trapezoidal shape. Moreover, in certain embodiments, the implants of the present invention may incorporate the use of sutures or with other types of surgically implantable structures and the like to facilitate attachment of the same into position. Specifically, it is contemplated that such embodiments may rely upon a combination of structures in combination with certain portions of the implant to facilitate attachment and positioning thereof.

For purposes of defining the general parameters of implants of the present invention, it is presently believed that the support portion of the implant will define a surface area ranging from a 1 cm width by 2 cm length to an 8 cm width by 8.0 cm length. With respect to the anchor portion, the same will preferably define a surface area defined by a 0.5 cm width by 5.0 cm length to an area defined by a 4.0 cm width to a 45.0 cm length. With respect to the latter, it should further be understood that certain embodiments of the present invention, discussed more fully below, sutures may be utilized in operative combination with the anchoring portion or, in certain embodiments, exclusively with the support portion, to thus define means for attaching and securing the implant into position.

With respect to the fabrication of the implants of the present invention, the same may be made from either synthetic materials, such as surgical mesh and the like, natural tissues, such as tissues harvested from either an animal, cadaverous source or the patient himself, and/or combinations of synthetic and natural materials. Along these lines, it is contemplated that the implants of the present invention can be fabricated consistent with those methods disclosed in Applicant's co-owned and co-pending U.S. patent application Ser. No. 10/684,861, the teachings of which are expressly incorporated herein by reference. Along these lines, it is further contemplated that in certain embodiments of the present invention, the implants may be prefabricated with slings or sutures attached thereto, consistent with the teachings of Applicants' co-owned pending U.S. patent application Ser. No. 10/947,182, entitled READILY IMPLANTABLE SLING, the teachings of which are likewise incorporated by reference.

Bearing the foregoing principles in mind, a detailed explanation is provided herebelow with respect to the structure, properties and functioning of the implants of the present invention. Referring again to FIG. 1, the implant 10 is situated such that the support portion 12 thereof is operatively positioned over the urethra. The implant 10 as depicted includes first and second support portions 14, 16 that are shown extending through the obturator foramen 18 and wrapped about dedicated ones of the descending rami 20, 22 of hip bones 24, 26, respectively.

Figure 2:
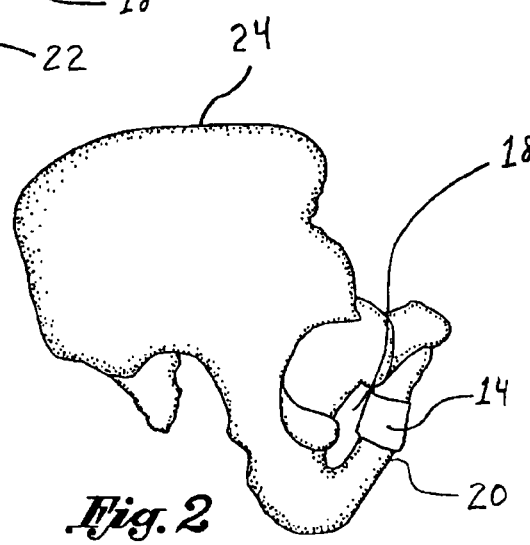
FIG. 2 is a side perspective view of the pelvis and implant of FIG. 1 showing a respective one of the anchor portions of the implant secured about the ramus.

FIG. 2 more clearly depicts such engagement between a respective one of the anchor portions 14 as extending through the obturator foramen 18 and engaged with descending ramus 20 of hip bone 24. In this regard, the implants of the present invention generally operate on the principle of including attachment of the implant into position via an anchoring mechanism that extends through the obturator foramen and becoming secured to at least one, and preferably both of the descending ramus of the patient; however, it should be understood that the descending ramus locus is not to limit the scope of the present invention and that attachment to any part of the periphery of the pubis and ischium may be considered suitable areas to which the implants of the present invention may be attached. Accordingly, fixation of the anchor portions at the descending rami or any other structure should not be deemed limiting in any respect.

Figure 3:
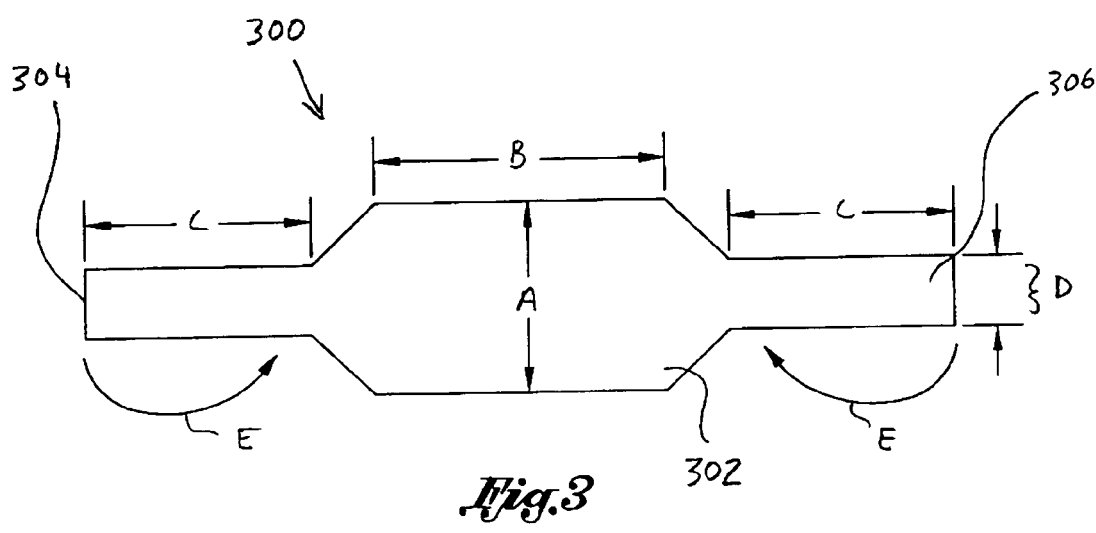
FIG. 3 is a frontal view of an implant for the treatment of male urinary incontinence as constructed in accordance with the present invention.

Bearing the foregoing principles in mind, and referring now to remaining FIGS. 3-9, there are shown various embodiments of the implants of the present invention. Referring initially to FIG. 3, implant 300 is defined by support portion 302 with anchor portions 304, 306 extending in opposed directions therefrom. According to a preferred embodiment, support portion will have a width "A" of approximately 4 cm and a length "B" of approximately 6 cm. Anchor portions 304, 306 may extend from support portion 302 via a tapered segment, as shown, and will have a length "C" of approximately 15 cm and a width "D" of approximately 2 cm. As discussed above, the implant 300 may be fabricated from either synthetic and/or natural materials. It should be understood, however, that the specific dimensions provided herein are not absolute, and variations in the length and width of both the support portion 302 and anchor portions 304, 306 can be readily made by those skilled in the art. Along these lines, it should be understood that the specific dimensions provided herein can vary by 50% or substantially greater, as discussed above, and retain its ability for use as an implant.

With respect to the procedure for implanting the implant 300 depicted in FIG. 3, Applicants believe that the best mode for performing the same will require the patient to assume a lithotomy position. A vertical perineal incision will be made in the midline dissecting to expose the bulbar urethra in the inferior aspect of the descending rami bilaterally. A suitable introducer is then passed from inside out or outside in through the upper aspect of the obturator foramen. A suture that is attached to a respective one of the anchor portions 304 or 306 is threaded through the introducer. The introducer is then retracted and the suture is pulled until a respective one of the ends of the anchor portion 304 or 306 to which the suture is attached can be grasped. The support portion 302 is then carried over the bulbar urethral complex and, thereafter, a second introducer is passed from inside out or outside in on the contra-lateral side to thus enable the second other respective anchor portion extends through the obturator foramen. The second introducer is then retracted and a suture affixed to the respective other anchor portion extends around the pubic ramus. Once so positioned, tension is introduced to the implant 300 such that the support portion 302 thereof achieves optimal suburethral compression. The respective ends of anchor portions 304, 306 are then secured, preferably via attachment to support portion 302 at the edge of each pubic ramus. To achieve that end, it is contemplated that a suture with or without an additional tensioning disc (not shown) is passed through anchor portions 304, 306 to effectuate such attachment.

Figures 4, 5:
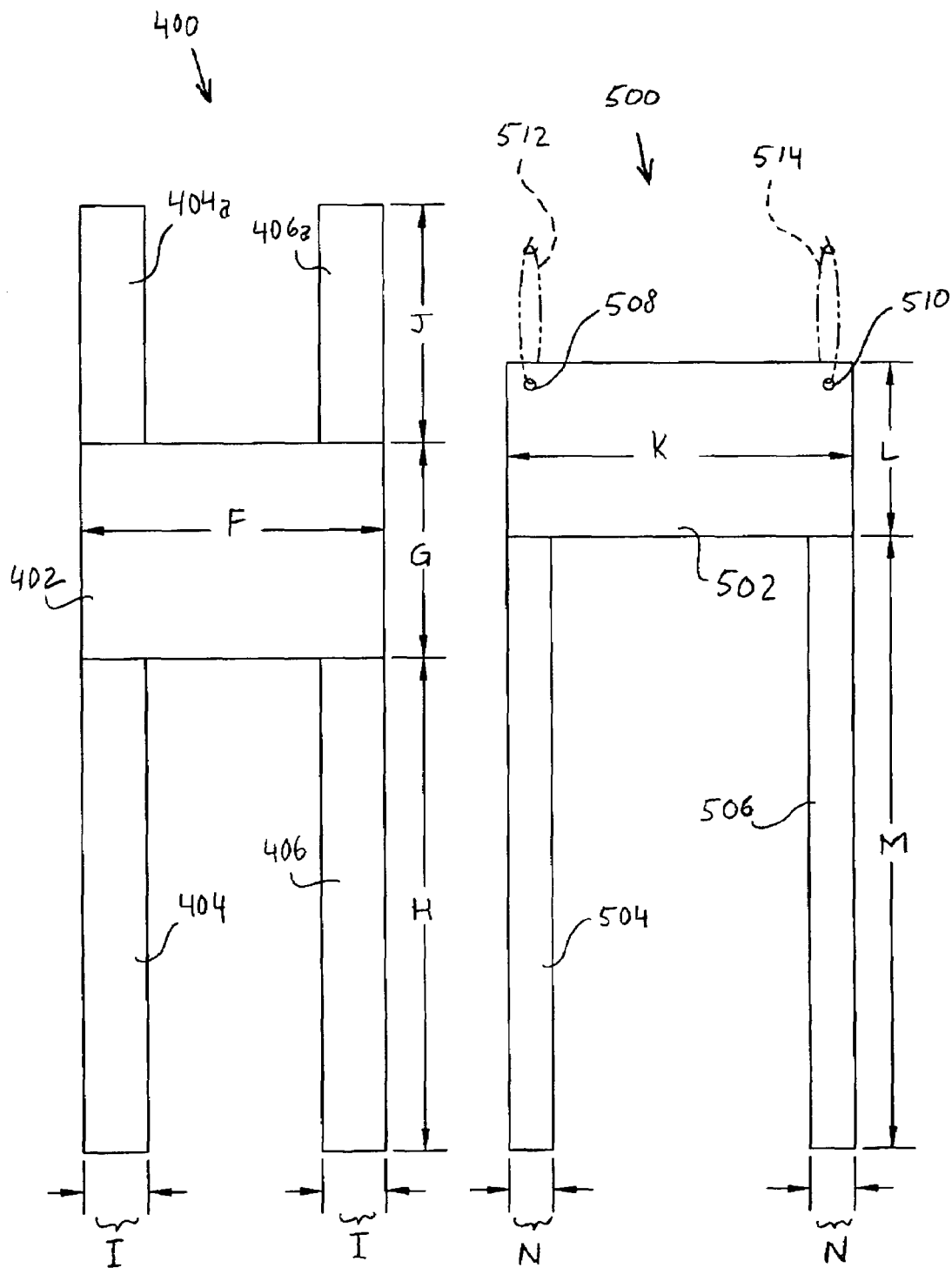
FIG. 4 is a frontal view of an implant for the treatment of male urinary incontinence as constructed in accordance with another embodiment of the present invention.
FIG. 5 is a frontal view of an implant for the treatment of male urinary incontinence as constructed in accordance with another embodiment of the present invention.

Referring now to FIG. 4, there is shown a further embodiment 400 for use in the surgical treatment of male urinary incontinence. As depicted, the implant 400 includes a support portion 402 with first and second anchor portions 404, 406 depending therefrom in generally parallel relation to one another and additional anchor portions 404a, 406a, ascending therefrom to define an "H" shape. The implant 400, as depicted, is preferably formed such that support portion 402 has a width "F" of approximately 7 cm and a height "G" of approximately 5 cm. Anchor portions 404, 406 preferably have a length "H" of approximately 30 cm and a width "I" of 1 cm. Additional anchor portions 404a, 406a will have a width of approximately 1.5 cm and a height "J" of approximately 14 cm, and may preferably be formed as extensions of 404 and 406, respectively. Again, such dimensions can be varied as may be deemed appropriate by one skilled in the art.

In the embodiment depicted, anchor portions 404, 406 are operative to extend through the retropubic space, from posterior to symphysis, or may extend via a transobturator route. Anchor portions 404a, 406a are operative to pass through the rectus fascia from anterior to symphysis.

Per the best mode discussed above with respect to implant 300, the surgical procedure for implanting implant 400 will preferably be conducted with the patient assuming a lithotomy position whereby a vertical perineal incision will be made in the midline dissecting to expose the bulbar urethra in the descending pubic rami bilaterally. The bulbar spongiosis will be left intact. Thereafter, suprapubic transverse incisions of approximately 1 cm are made, 3 cm lateral to the midline on either side. A suitable introducer is then passed from such incisions and tunneled superficially anterior to the pubic symphysis (not retropubically) and caused to exit through the initial perineal incision. A respective one of the ascending anchor portions 404a or 406a is attached to a suprapubic introducer and pulled through the suprapubic incisions. This same maneuver is then repeated for the respective other ascending anchor portion 404a or 406a.

Hereafter, two new incisions, which are preferably approximately 1 cm above the pubic symphysis are performed. The suitable introducer is then passed from above, retropubically, and out through the initial perineal incision. A respective one of the descending anchor portions 404 or 406 is then attached to the introducer and pulled up through such newly formed incision. Such procedure is repeated with respect to the other descending anchor portion 404 or 406, which as a consequence creates two sets of anchor portions, namely, descending anchor portions 404, 406 and ascending portions 404a, 406a in the suprapubic region. The ascending anchor portions 404a, 406a are then tunneled into the retropubic anchor portions 404, 406 beneath the skin and thereafter ascending portion 404a will be surgically connected with descending portion 404 and ascending portion 406a surgically attached to descending anchor portion 406. To achieve such surgical attachment, it is contemplated that such attachment may be attained via the use of sutures.

In a further refinement of such procedure, it is contemplated that surgical positioning of descending anchor portions 404, 406 can be accomplished via the use of a suitable introducer that is passed from outside in or inside out through the obturator foramen. A suture that is attached to the distal most end of respective one of anchor portions 404, 406 will be threaded to the introducer. Once the introducer is advanced through the obturator foramen, the same is retracted with the suture affixed to the end of descending anchor portion 404 or 406 is pulled until the end of the anchor portion 404 or 406 can be grasped. A second suitable introducer is utilized with respect to the surgical positioning of the respective other anchor portion 404 or 406 on the contra-lateral side. Once so positioned, anchor portions 404 and 406 can be affixed to ascending anchor portions 404a, 406a around the descending rami via the transobturator approach and secured on itself via a suture line.

Referring now to FIG. 5, there is shown a further embodiment of an implant 500 falling within the scope of the present invention. As depicted, the implant includes a support portion 502 and first and second support portions 504, 506 depending therefrom in generally parallel relation to define an inverted U-shape. The support portion 502 further includes first and second apertures 508, 510 formed thereon through which dedicated sutures 512, 514 extend therethrough. The implant 500 is preferably fashioned such that the support portion 502 has a length "K" of approximately 8 cm and a height "L" of approximately 4 cm. Each respective anchor portion 504 will preferably have a length "M" of approximately 45 cm in length and a width "N" of approximately 1 cm in length. Again, the dimensions of such implant can vary as will be understood by those skilled in the art.

With respect to the implantation of the implant 500, the same is again performed with the patient assuming lithotomy position. A vertical perineal incision is made in the midline dissecting to expose the bulbar urethra and the descending rami bilaterally leaving the bulbar spongiosis intact. One centimeter suprapubic transverse incisions are made 3 cm laterally to the midline on either side. A suitable introducer is then passed from this "stab wound" and tunneled superficially anterior to the pubic symphysis (not retropubically) that exits through the initial perineal incision. A respective one of the sutures 512 or 514 is attached to the introducer and pulled through the upper "stab" incision. This same procedure is repeated on the respective other side with respective other suture 512 or 514. Respective ones of the sutures 512, 514 are tied down to the rectus fascia in the suprapubic area.

A suitable introducer is then passed from outside in or inside out through the obturator foramen. A suture that is attached to a respective one of the anchor portions 504 or 506 on one side is threaded through such introducer. The introducer is retracted and the suture is pulled until the respective one of the ends of either 504, 506 (depending on which portion is attached) can be grasped. The same procedure is repeated with respect to the other anchor portion 504 or 506 whereby a second introducer is passed from outside in or inside out on the contra-lateral side. Both free ends of anchor portions 504 or 506 will be overlapped and secured. Along these lines, such anchor portions 504, 506 will be tied around the descending rami via a transobturator approach and thus secured to itself via a suture.

In a variation of the embodiment and procedure discussed above with respect to implant 500, it is contemplated that as opposed to the use of apertures 508, 510 with dedicated suture lines 512 and 514 affixed thereto, the implant 500 may utilize thumb tack-like anchors (not shown) in the positions of 508 and 510, respectively. Such embodiment will further preferably include a support portion 502 that has a width "K" of 7 cm as opposed to 8 cm.

To implant such embodiment, the patient will assume a lithotomy position and a vertical perineal incision will be made in the midline dissecting to expose the bulbar urethra and descending rami bilaterally leaving the bulbar spongiosis intact. The support portion 502 will be attached via these thumb tacks positioned where apertures 508 and 510 are depicted, respectively, on each side of the upper aspect of the descending rami close to the pubic symphysis.

A suitable introducer is then passed from outside in or inside out through the obturator foramen. A suture that is attached to a respective distal-most end of one of the anchor portions 504 or 506 is threaded through the introducer. The introducer is then retracted and the suture is pulled until the distal-most end of a respective one of one of the anchor portions 504 or 506 can be grasped. This portion of a respective one of the anchor portions is wrapped around the ramus and tied down to the support portion. A second introducer is passed from outside in or inside out on the contra-lateral side and the process is repeated with respect to the respective other anchor portion 504 or 506. The support portion 502 is then tacked down at the upper aspect of the descending rami. The anchor portions 504, 506 are then tied around the descending rami via the transobturator approach and then secured on itself via suture attachment.

Figure 6:
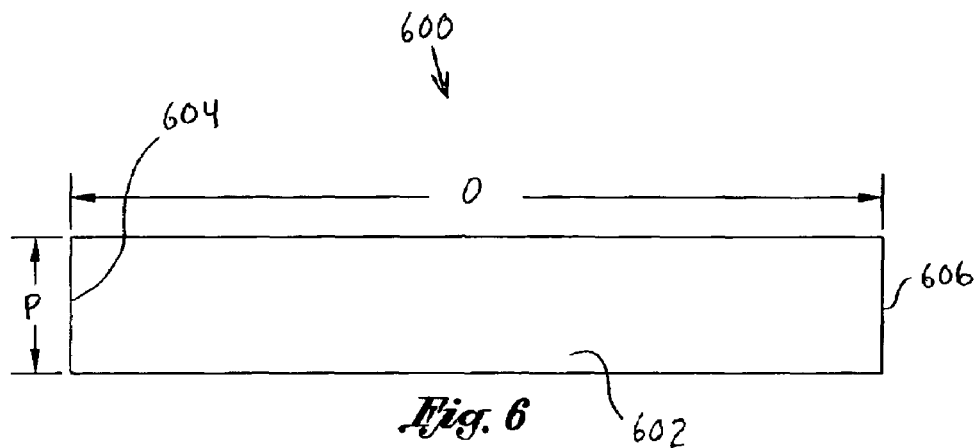
FIG. 6 is a frontal view of an implant for the treatment of male urinary incontinence as constructed in accordance with another embodiment of the present invention.

Referring now to FIG. 6, a further implant 600 is depicted. As illustrated, the implant 600 comprises a generally rectangular implant defining a middle support portion 602 with anchor portions 604, 606 formed integral therewith and defining first and second opposed ends. According to such implant, the same will preferably be formed to have a length "O" of approximately 45 cm and a width "P" of approximately 3 cm.

To implant such embodiment 600, a vertical perineal incision is made in the midline dissecting to expose the bulbar urethra and the inferior aspect of the descending rami bilaterally while the patient assumes a lithotomy position. A suitable introducer is passed from outside in or inside out through a 3 cm groin incision that is chosen with the finger in the initial perineal incision to pass through the obturator foramen. A respective end 604 or 606 that is attached to the introducer tip and advanced within the perineal incision. The introducer is retracted through the obturator foramen with the respective other end 604 or 606 being grasped at the lateral groin incision site and cut at skin level. The opposite end 604 or 606 is carried over the bulbar urethral complex. A second suitable introducer is passed from outside in or inside out through another 3 cm groin incision on the contra-lateral side and the process is repeated. The respective ends 604 and 606 of the implant 600 are cut at the level of the skin at the groin incisions.

Figure 7:
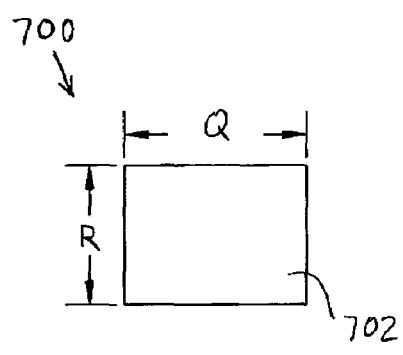
FIG. 7 is a frontal view of an implant for the treatment of male urinary incontinence as constructed in accordance with another embodiment of the present invention.

The implant in embodiment 700 depicted in FIG. 7 assumes a generally rectangular configuration having a width "Q" of 4 cm and a height "R" of 3 cm. Per the other embodiments, the implant is preferably secured into position by making a vertical perineal incision to the midline dissecting to expose the bulbar urethra and the inferior aspect of the descending rami bilaterally while the patient assumes a lithotomy position. A suture secured on a UR-6 needle is then used to bite into the periosteum of the descending rami bilaterally. Although not shown, there will be four sutures altogether on each side for a total of 8 secured knots to fix the implant 700 into position. The lower three sutures on one side are threaded through the implant, which is placed as high as possible on the bulbar urethral complex. Such lower three sutures are loosely held to stabilize the sling and the top apical suture is then placed, one on each side at the junction of the descending rami to the pubic symphysis. The apical sutures are tied down as tight as possible. The three lower sutures are then tied down accordingly on each side.

Figure 8:
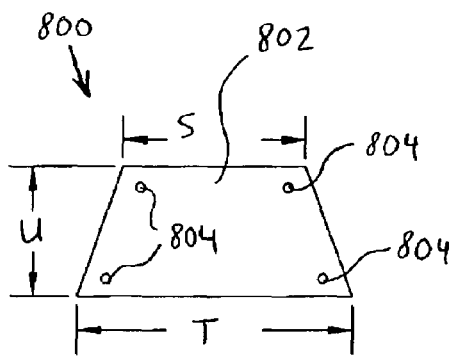
FIG. 8 is a frontal view of an implant for the treatment of male urinary incontinence as constructed in accordance with another embodiment of the present invention.

In the further embodiment depicted in FIG. 8, the implant 800 assumes a generally trapezoidal having an upper length "S" of approximately 4 cm, a lower length "T" of approximately 6 cm and a height "U" of approximately 3 cm. Such implant is secured in position via the initial formation of a vertical perineal incision that is made in the midline dissecting to expose the bulbar urethra and the descending rami bilaterally leaving the bulbar spongiosis intact. The implant 800, which will further preferably have access holes 804 formed thereon, is then placed over the bulbar urethra complex. A fine drill, such as many of a variety well-known to those skilled in the art, is then advanced through each of the holes 804 to secure a preloaded suture. The four sutures that will extend through dedicated ones of the apertures 804 are tied along side of the lateral aspects of the implant 802 to create two knots on each side. The support portion 802 will then be operative to provide the necessary degree of suburethral support.

Figure 9:
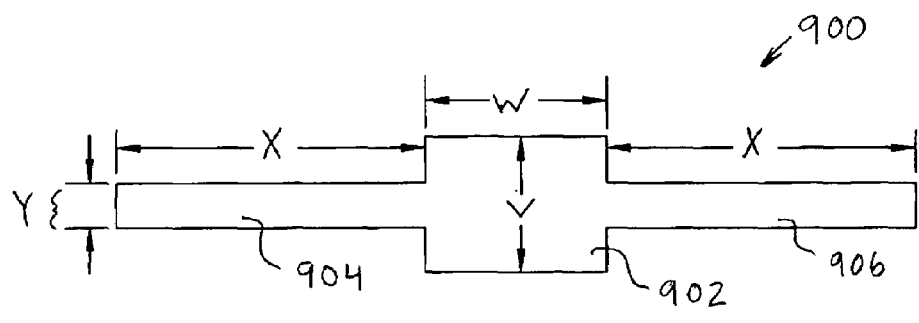
FIG. 9 is a frontal view of an implant for the treatment of male urinary incontinence as constructed in accordance with another embodiment of the present invention.

In FIG. 9, there is depicted yet a further embodiment of an implant 900 useful in the surgical treatment of male urinary incontinence and falling within the scope of the present invention. Such implant will preferably have the dimensions of a height "V" of 3 cm and a width of 4 cm, as the same pertains to the urethral support portion 902. Each anchor portion 904, 906 will preferably have a length "X" of approximately 20 cm and a width "Y" of 1 cm. Similar to the embodiment depicted in FIG. 3, such embodiment 900 includes a urethral support portion 902 with two anchor portions 904, 906 extending therefrom in opposed directions. With regard to the best mode by which Applicants would suggest securing such implant 900 into position, such surgical procedure would involve the patient assuming a lithotomy position and, per the other embodiments discussed above, a vertical perineal incision would be made in the midline dissecting to expose the bulbar urethral and the inferior aspect of the descending rami bilaterally. A suitable introducer would then be passed from inside out or outside in through the upper aspect of the obturator foramen. An end portion of a respective one of the anchor portions 904 or 906 is attached through the introducer. The introducer is retracted and the respective other end of the respective other anchor portion 904 or 906 is grasped and a ratchet closure is done, as will be understood by those skilled in the art. Support portion 902 is carried over the bulbar urethral complex. Thereafter, a second suitable introducer is passed from inside out or outside in on the contra-lateral side and the process repeated with respect to the other respective anchor portion 904, 906. The ends of the sling are then secured to a square-like portions of the urethral support portion 902 at the edge of the pubic ramus with a ratchet closure.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention. Along these lines, the suggested surgical implantation techniques with respect to each of the depicted embodiments simply represents the Applicants' best mode for practicing the invention. It should be understood, however, that different surgical approaches may be readily known and understood by those skilled in the art. In addition, it is contemplated that future advances in medicine can and will be made that will facilitate the ability of the implants of the present invention to be more easily, quickly and accurately secured into position and operative to achieve the highest degree of favorable patient outcome. In addition, it is emphasized again that although dimensions are provided herein with respect to the implants of the present invention, as well as the choice of materials that may be utilized as to fabricate the same, it should be understood that any suitable material useful for fabricating an implant, whether known now or later developed, should be deemed to fall within the scope of the present invention.

What is claimed is:

1. A method of treating incontinence in a male patient comprising:
   providing an implant;
   making a non-scrotal perineal incision in said male patient;
   placing a portion of said implant through said perineal incision and through each obturator foramen of said male patient and around a descending ramus of said male patient; and
   placing a portion of said implant through said perineal incision upwardly toward rectus fascia of said male patient.

2. A method according to claim 1, wherein said implant includes a main section, a first pair of arms, and a second pair of arms.

3. A method according to claim 2, wherein placing a portion of said implant through each obturator foramen of said male patient includes placing one of said first pair of arms through each obturator foramen of said male patient.

4. A method according to claim 2, wherein said main section is a mesh material, said first pair of arms is a mesh material and said second pair of arms are comprised of a suture material.

5. A method of treating incontinence in a male patient comprising:
   providing an implant;
   making a non-scrotal perineal incision in said male patient;
   placing a portion of said imlant through said perineal incision and through each obturator foramen of said human and around a descending ramus of said male patient;
   placing a portion of said implant through said perineal incision upwardly toward rectus fascia of said male patient; and
   placing a portion of said implant through said perineal incision upwardly toward rectus fascia of said male patient anterior to a symphysis of said male patient.

6. A method of treating incontinence in a male patient comprising:
   providing an implant;
   making a non-scrotal perineal incision in said male patient; and
   placing a portion of said implant through said perineal incision and through each obturator foramen of said male patient and around a descending ramus of said male patient,
   wherein said implant includes a main section, a first pair of arms, and a second pair of arms, and wherein placing a portion of said implant upwardly toward rectus fascia of said male patient includes placing each of said second pair of arms of said implant upwardly toward said rectus fascia.

7. A method of treating incontinence in a human comprising:
   providing an implant including a main section, a first pair of arms, and a second pair of arms, wherein said each of said first pair of arms has (i) a proximal end adjacent to said main section of said implant and (ii) a distal end opposite from said proximal end;
   making a perineal incision in said human;
   placing a portion of said implant through said perineal incision and through each obturator foramen of said human and around a descending ramus of said human, including placing one of said first pair of arms through each obturator foramen of said human; and
   connecting the distal ends of each of said first pair of arms to said main section of said implant after placing each of said first pair of arms around said descending ramus.

8. A method according to claim 7, wherein connecting the distal ends of each of said first pair of arms to said main section includes suturing the distal ends of each of said first pair of arms to said main section of said implant.

9. A method of treating incontinence in a male patient comprising:
   providing an implant;
   making a non-scrotal perineal incision in said male patient; and
   placing a portion of said implant through said perineal incision and through each obturator foramen of said male patient and around a descending ramus of said male patient,
   wherein said implant includes a main section, a first pair of arms, and a second pair of arms, and wherein said main section is a mesh material, said first pair of arms is a mesh material, and said second pair of arms is a mesh material.

10. A method of treating urinary incontinence comprising:
    providing an implant;
    making an incision exposing a urethral region in a patient;
    advancing said implant towards said exposed urethral region;
    extending a first portion of said implant through an obturator foramen of said patient, around an ischiopubic ramus of said patient and back to said urethral region;
    extending a second portion of said implant through the other obturator foramen of said patient, around the ischiopubic ramus of said other obturator foramen of said patient and back to said urethral region; and
    extending a third and fourth portion of said implant upwardly toward a suprapubic region of said patient.

11. A method according to claim 10, further comprising extending a third and fourth portion of said implant upwardly toward a suprapubic region of said patient on opposite sides, respectively, of a midline of said patient.

12. A method according to claim 11, further comprising extending a third and fourth portion of said implant upwardly toward a suprapubic region of said patient on opposite sides, respectively, of a midline of said patient at a location anterior to said symphysis of said patient.

13. A method according to claim 10, further comprising positioning a support portion of said implant in said urethral region of said patient.

14. A method according to claim 13, further comprising securing said first and second portions of said implant to said support portion of said implant.

15. A method according to claim 10, wherein the first, second, third and fourth portions of said implant are a mesh material.

16. A method according to claim 10, wherein making an incision exposing a urethral region comprises making a perineal incision.

17. A method according to claim 10, wherein the extending of said first portion of said implant through an obturator foramen of said patient, around an ischiopubic, ramus of said patientand back to said urethral region comprises:
  attaching said first portion to an inside-out transobturator tool; and,
  urging said inside-out transobturator tool through said obturator foramen and back towards said incision.

18. A method according to claim 17, wherein the extending of said second portion of said implant through an obturator foramen of said patient, around an ischiopubic ramus of said patient and back to said urethral region comprises:
  attaching said second portion to an inside-out transobturator tool; and,
  urging said inside-out transobturator tool through said obturator foramen and back toward said incision.

19. A method according to claim 10, wherein the extending of said first portion of said implant through an obturator foramen of said patient, around an ischiopubic ramus of said patient and back to said urethral region comprises:
  urging an outside-in transobturator tool through said obturator foramen;
  attaching said first portion to an outside-in transobturator tool; and,
  withdrawing said outside-in transobturator tool through said obturator foramen and back toward said incision.

20. A method according to claim 19, wherein the extending of said second portion of said implant through an obturator foramen of said patient, around an ischiopubic ramus of said patient and back to said urethral region comprises:
  urging an outside-in transobturator tool through said obturator foramen;
  attaching said second portion to an outside-in transobturator tool; and,
  withdrawing said outside-in transobturator tool through said obturator foramen and back toward said incision.

* * * * *